United States Patent
Kirsch et al.

(10) Patent No.: US 9,746,458 B2
(45) Date of Patent: Aug. 29, 2017

(54) DYNACTIN SUBUNIT P62 BIOMARKER FOR NEUROLOGICAL CONDITIONS

(75) Inventors: Wolff M. Kirsch, Redlands, CA (US); Matthew Schrag, Grand Terrace, CA (US); Andrew Crofton, Loma Linda, CA (US); Matthew Zabel, Loma Linda, CA (US); Claudius Mueller, Warrenton, VA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 13/457,352

(22) Filed: Apr. 26, 2012

(65) Prior Publication Data
US 2012/0331573 A1    Dec. 27, 2012

Related U.S. Application Data

(60) Provisional application No. 61/479,796, filed on Apr. 27, 2011.

(51) Int. Cl.
*G01N 33/50* (2006.01)
*G01N 33/566* (2006.01)
*G01N 33/84* (2006.01)

(52) U.S. Cl.
CPC ....... *G01N 33/5058* (2013.01); *G01N 33/566* (2013.01); *G01N 33/84* (2013.01); *G01N 2500/10* (2013.01); *G01N 2800/2821* (2013.01)

(58) Field of Classification Search
CPC ........... C12Q 1/6886; C12Q 2600/158; C12Q 2600/106; C12Q 1/6883; C12Q 2600/136; C12Q 2600/112; C12Q 2600/118; C12Q 2600/156; C12Q 1/6806; C12Q 2600/178; C12Q 1/6809; C12Q 1/6837; C12Q 1/6876; C12Q 1/6895; C12Q 2537/164; C12Q 2563/161; C12Q 2600/154; C12Q 1/485; C12Q 2600/172; G01N 2500/10; G01N 2800/2821; G01N 33/5058; G01N 33/566; G01N 33/84; G01N 33/57484; G01N 33/574; G01N 33/57496; G01N 33/6893;
(Continued)

(56) References Cited

U.S. PATENT DOCUMENTS 6,720,138 B2 * 4/2004 Sharma et al. .............. 435/6.16
2004/0146937 A1 * 7/2004 Rich et al. .................... 435/7.1
(Continued)

FOREIGN PATENT DOCUMENTS

WO    WO/2007/038523 A2    4/2007
WO    WO 2008063369 A2 *  5/2008
(Continued)

OTHER PUBLICATIONS

Liang et al. (Physiol Genomics 2008 vol. 33 pp. 240-256).*
(Continued)

*Primary Examiner* — Joseph G Dauner
(74) *Attorney, Agent, or Firm* — Knobbe Martens Olson & Bear LLP

(57) ABSTRACT

Methods and kits for identifying neurological conditions in a patient by determining a level of expression of dynactin subunit p62 are disclosed. The neurological conditions may include, for example, Alzheimer's Disease (AD) without cerebral amyloid angiopathy (CAA).

8 Claims, 3 Drawing Sheets

(58) Field of Classification Search
CPC ......... G01N 33/6896; G01N 2333/705; G01N 2500/10

See application file for complete search history.

(56) References Cited

U.S. PATENT DOCUMENTS

2006/0257903 A1\* 11/2006 Akil et al. .................... 435/6
2010/0209417 A1\* 8/2010 Lee et al. .................. 424/133.1

FOREIGN PATENT DOCUMENTS

WO   WO/2008/115653 A2   9/2008
WO   WO 2011/028960   \*   3/2011

OTHER PUBLICATIONS

Moftakhar (J Neuropathol Exp Neurol Dec. 2010 vol. 69 No. 12 pp. 1201-1209).\*

Schrag. "Cerebral Amyloid Angiopathy and Transition Metals in Alzheimer's Disease" (2010). Loma Linda University Electronic Theses & Dissertations. Paper 10.\*

Andersen, L., and C.L. Hunter, "Quantitative Mass spectrometric Multiple Reaction Monitoring Assays for Major Plasma Proteins," Molecular & Cellular Proteomics 5.4:573-588, 2006.

Bitter, G.A., et al., "Expression and Secretion Vectors for Yeast," Methods in Enzymology 153:516-444, 1987.

Borrebaeck, C.A.K., and C. Wingren, "High-throughput proteomics using antibody microarrays: an update," Expert Rev. Mol. Diagn. 7(5):673-686, 2007.

Brisson, N., et al., "Expression of a Bacterial Gene in Plants by Using a Viral Vector," Nature 310:511-514, 1984.

Broglie, R., et al., "Light-Regulated Expression of a Pea Ribulose-1,5-Bisphosphate Carboxylase Small Subunit Gene in Transformed Plant Cells," Science 224:838-843, 1984.

Castaño, E.M., et al., "Comparative Proteomics of Cerebrospinal Fluid in Neuropathologically-Confirmed Alzheimer's Disease and Non-Demented Elderly Subjects," Neurol. Res. 28:1155-163, 2006.

Coruzzi, G., et al., "Tissue-Specific and Light-Regulated Expression of a Pea Nuclear Gene Encoding the Small Subunit of Ribulose-1,5-Biphosphate Carboxylase," EMBO J. 3(8):1671-1680, 1984.

De Bie, P., et al., "Molecular Pathogenesis of Wilson and Menkes Disease: Correlation of Mutations With Molecular Defects and Disease Phenotypes," J. Med. Genet. 44:673-688, 2007.

Dingwall, C., "A Copper-Binding site in the Cytoplasmic Domain of BACE1 Identifies a Possible Link to Metal Homeostasis and Oxidative Stress in Alzheimer's disease," Biochem. Soc. 35(3):571-573, 2007.

Domon, B., and R. Aebersold, "Mass Spectrometry and Protein Analysis," Science 312:212-217, 2006.

Fahrlander, P.D., and A. Klausner, "Amplifying DNA Probe Signals: A 'Christmas Tree' Approach," Bio/Technology 6:1165-1168, 1988.

Gurley, W.B., et al., "Upstream Sequences Required for Efficient Expression of a Soybean Heat Shock Gene," Mol. Cell. Biol. 6(2):559-565, 1986.

Hayward, L.J., et al., "Decreased Metallation and Activity in Subsets of Mutant Superoxide Dismutases Associated With Familial Amyotrophic Later Sclerosis," J. Biol. Chem. 277:15923-15931, 2002.

Kimura, N., et al., "Aging Attenuates Dynactin-Dynein Interaction: Down-Regulation of Dynein Causes Accumulation of Endogenous Tau and Amyloid Precursor Protein in Human Neuroblastoma Cells," J. Neurosci. Res. 85:2909-2916, 2007.).

Kimura, N., et al., "Dynein Dysfunction Induces Endocytic Pathology Accompanied by an Increase in Rab Gtpases: A Potential Mechanism Underlying Age-Dependent Endocytic Dysfunction," J. Biol. Chem. 284(45):31291-31302, 2009.

Kurosawa, S., et al., "Quartz Crystal Microbalance Immunosensors for Environmental Monitoring," Biosensors & Bioelectronics 22(4):473-481, 2006.

Lee, L.J., et al., "Microfluidic Enzyme-Linked Immunosorbent Assay Technology," Adv. Clin. Chem. 42:255-259, 2006.

Leiva, J., et al., "Copper Interaction on the Long-Term Potentiation," Arch. Ital. Biol. 141(2-3):149-155, 2003.

Lim, C.M., et al., "Copper-Dependent Interaction of Dynactin Subunit p62 With the N Terminus of ATP7B but not ATP7A," J. Biol. Chem. 281(20):14006-14014, 2006.

Lin, J., et al., "Electrochemical Immunosensor for Carcinoembryonic Antigen Based on Antigen Immobilization in Gold Nanoparticles Modified Chitosan Membrane," Analytical Sciences 23(9):1059-1063, 2007.

Lindsey, J.C., et al., "Epigenetic Deregulation of Multiple S100 Gene Family Members by Differential Hypomethylation and Hypermethylation Events in Medulloblastoma," British Journal of Cancer 97(2):267-274, 2007.

Liotta L. and E.F. Petricoin, "Serum Peptidome for Cancer Detection: Spinning Biologic Trash Into Diagnostic Gold," J. Clin. Invest. 116(1):26-30, 2006.

Lopresti, B.J., et al., "Simplified Quantification of Pittsburg Compound B Amyloid Imaging PET Studies: A Comparative Analysis," J. Nucl. Med. 46:1959-1972, 2005.

Lovell, M.A., et al., "Copper, Iron and Zinc in Alzheimer's Disease Senile Plaques," J. Neur. Sci. 158:47-52, 1998.

Macreadie, I.G., "Copper Transport and Alzheimer's Disease," Eur. Biophys. J. 37:295-300, 2008.

Maeda, M., and O. Hino, "Blood Tests for Asbestos-Related Mesothelioma," Oncology 71:26-31, 2006.

Mueller, C, et al., "The Heme Degradation Pathway is a Promising Serum Biomarker Source for the Early Detection of Alzheimer's Disease," J. Alz. Dis. 19:1081-1091, 2010.

Museth. A.K., et al., "The ALS-Associated Mutation G93A in Human Copper-Zinc Superoxide Dismutase Selectively Destailizes the Remote Metal Binding Region," Biochem. 48:8817-8829, 2009.

Narindrasorasak, S., et al., "Protein Disulfide Isomerase, A Multifunctional Protein Chaperone, Shows Copper-Binding Activity," Biochem. Biophys. Res. Commun. 311:405-414, 2003.

Naya, et al., "Evaluation of Precursor Prostate-Specific Antigen Isoform Ratios in the Detection of Prostate Cancer," Urologic Oncology 23(1):16-21, 2005.

Nedelkov, "Development of Surface Plasmon Resonance Mass Spectrometry Array Platform," Anal. Chem. 79(15):5987-5990, 2007.

Nedelkov, D., "Mass Spectrometry-Based Immunoassays for the Next Phase of Clinical Applications," Expert Rev. Proteomics, 3(6):631-640, 2006.

Ohsawa K., et al., "New Fractionation Method of Synaptic Vesicles in the Brain," Proc. Japan Acad. 51:202-208, 1975.

Petersen, R.C., et al., "Mild Cognitive Impairment: Clinical Characterization and Outcome," Arch. Neurol. 56:303-308, 1999.

Petersen, R.C., "Mild Cognitive Impairment as a Diagnostic Entity," J. Intern. Med. 256:183-194, 2004.

Pluckthun, A., "The Pharmacology of Monoclonal Antibodies," Rosenburg and Moore, Eds., Springer-Verlag, New York, pp. 269-315, 1994.

Reisberg, B., "Global Measures: Utility in Defining and Measuring Treatment Response in Dementia," Int. Psychogeriatr. Assoc. 19(3):421-456, 2007.

Renberg, B., et al., "Affibody Molecules in Protein Capture Microarrays: Evaluation of Multidomain Ligands and Different Detection Formats," J. Proteome Res. 6(1):171-179, 2007.

Sambrook, J., et al., Molecular Cloning: A Laboratory Manual, $2^{nd}$ ed., Cold Spring Harbor Laboratory Press, pp. 18.7-18.18, 1989.

Schlief, M.L., et al., "Copper Homeostasis in the CNS: A Novel Link Between the NMDA Receptor and Copper Homeostasis in the Hippocampus," Mol. Neurobiol. 33:81-90, 2006.

Schrag, M., et al., "The Effect of Formalin Fixation on the Levels of Brain Transition Metals in Archived Samples," Biometals 23(6):1123-1127, 2010.

(56) References Cited

OTHER PUBLICATIONS

Schrag, M., et al., "Iron, Zinc and Copper in the Alzheimer's Disease Brain: A Quantitative Meta-Analysis. Some Insight on the Influence of Citation Bias on Scientific Opinion," Prog. Neurobiol. 94(3):296-306, 2011.

Schwenk, et al., "Determination of Binding Specificities in Highly Multiplexed Bead-Based Assays for Antibody Proteomics," Mol. Cell Proteomics 6(1):125-132, 2007.

Squitti, R., et al., "Ceruloplasmin (2-D Page) Pattern and Copper Content in Serum of Alzheimer Disease Patients," Biomarker Insights I:205-213, 2006.

Studier, F.W., et al., "Use of T7 RNA Polymerase to Direct Expression of Cloned Genes," Methods in Enzymology 185:60-89, 1990.

Takamatsu, N., et al., "Expression of Bacterial Chloramphenicol Acetyltransferase Gene in Tobacco Plants Mediated by TMV-RNA," EMBO J. 6:307-311, 1987.

van der Want, J.J.L., et al., "Tract-Tracing in the Nervous System of Vertebrates Using Horseradish Peroxidase and its Conjugates: Tracers, Chromogens and Stabilization for Light and Electron Microscopy," Brain Res. Protoc. 1:269-279, 1997.

VanMeter, A., et al., "Reverse-Phase Protein Microarrays: Application to Biomarker Discovery and Translational Medicine," Expert Rev. Mol. Diagn. 7(5):625-633, 2007.

Walter, G., et al., "High-Throughput Protein Arrays: Prospects for Molecular Diagnostics," Trends Mol. Med. 8(6):250-253 (2002).

Wang, X., et al., "Copper Binding Regulates Intracellular Alpha-Synuclein, Localization, Aggregation and Toxicity," J. Neurochem. 113:704-714, 2010.

Ward, E.S., et al., "Binding Activities of a Repertoire of Single Immunoglobulin Variable Domains Secreted From *Escherichia coli*," Nature 341:544-546, 1989.

Weissbach & Weissbach, Methods for Plant Molecular Biology, Academic Press, NY, Section VIII, pp. 421-463, 1988.

Whiteaker, J.R., et al., "Integrated Pipeline for Mass Spectrometry-Based Discovery and Confirmation of Biomarkers Demonstrated in a Mouse Model of Breast Cancer," J. Proteome Res. 6(10):3962-3975, 2007.

Wu, D., et al., "Copper (II) Promotes the Formation of Soluble Neurotoxic PrP Oligomers in Acidic Environment," J. Cell. Biochem. 111:627-633, 2010.

Zhang, J., et al., "Protemic Biomarker Discovery in Cerebrospinal Fluid for Neurodegenerative Diseases," J. Alzheimer's Disease 8:377-386, 2005.

\* cited by examiner

DYNACTIN SUBUNIT P62 BIOMARKER FOR NEUROLOGICAL CONDITIONS

RELATED APPLICATION

The present application claims the benefit of priority to U.S. Provisional Patent Application No. 61/479,796, filed Apr. 27, 2011, the entire disclosure of which is incorporated herein by reference in its entirety.

STATEMENT REGARDING FEDERALLY SPONSORED R&D

This invention was made, in part, with funding under NIH Grant No. AG 20948. The U.S. Government has certain rights in this invention.

BACKGROUND

Field of the Disclosure

Aspects of the disclosure relate to the fields of molecular biology and medicine. In particular, disclosed herein are methods for diagnosing neurological conditions in a patient using expression levels of biomarkers.

Description of the Related Technology

Alzheimer's disease (AD) is a progressive degenerative disease of the brain primarily associated with aging. AD is one of several disorders that cause the gradual loss of brain cells and is a leading cause of dementia. Clinical presentation of AD is characterized by loss of memory, cognition, reasoning, judgment, and orientation. Mild cognitive impairment (MCI) is often the first identified stage of AD. As the disease progresses, motor, sensory, and linguistic abilities also are affected until there is global impairment of multiple cognitive functions. These cognitive losses occur gradually, but typically lead to severe impairment and eventual death in the range of three to twenty years.

An early diagnosis of AD has many advantages including, for example, increased time to maximize quality of life, reduced anxiety about unknown problems, increased chances of benefiting from treatment and increased time to plan for the future. However, reliable and noninvasive methods for diagnosing AD are not available.

Alzheimer's disease is characterized by two major pathologic observations in the brain: neurofibrillary tangles (NFT) and beta-amyloid plaques, comprised predominantly of an aggregate of fragments known as Aβ peptides. Individuals with AD exhibit characteristic beta-amyloid deposits in the brain (beta-amyloid plaques) and in cerebral blood vessels (beta-amyloid angiopathy) as well as neurofibrillary tangles. Neurofibrillary tangles occur not only in Alzheimer's disease but also in other dementia-inducing disorders. On autopsy, presently the only definitive method of diagnosing AD, large numbers of these lesions are generally found in areas of the human brain important for memory and cognition.

While advances have been made in imaging beta-amyloid, (Lopresti, et al. J. Nucl. Med. (2005) 46:1959-1972), no serum biomarkers for AD are clinically available that can detect early stage AD, particularly at the stage of MCI. There are no validated biomarkers for confirming the diagnosis of a major neurodegenerative disorder or to monitor progression (Castano, et al. Neurol. Res. (2006) 28:1155-163).

Despite the enthusiasm for the use of proteomic technology to discover blood markers of AD, and decades of effort, progress towards identifying useful markers has been slow, possibly because putative high specificity AD markers are assumed to be in very low abundance because they are shed from small volumes of diseased tissue and are expected to be rapidly cleared and metabolized. In addition, researchers have avoided studying blood because the blood proteome is complicated by resident proteins such as albumin that can exist at a concentration many millions of times greater than the target low abundance biomarker. For this reason, researchers have focused on cerebrospinal fluid (CSF) as the target fluid for AD biomarkers (see Zhang et al., J. Alzheimer's Disease (2005) 8:377-3386). The CSF approach, however, has limited clinical application to routine screening. Moreover, the blood brain vascular circulation perfuses AD lesions with a higher efficiency, particularly in the case for amyloid angiopathy.

SUMMARY OF CERTAIN INVENTIVE ASPECTS

In one aspect, a method for diagnosing Alzheimer's Disease (AD) in a subject is provided. The method includes, for example, obtaining a biological sample from a subject suspected of being at risk for said AD, determining a level of expression of dynactin, and comparing the level to a predetermined level indicative of a subject not having AD. In some embodiments, an increase in said detected level compared to the predetermined level indicates a greater likelihood of AD.

In some embodiments, the dynactin is subunit p62. In some embodiments, Alzheimer's Disease is without cerebral amyloid angiopathy (CAA).

In some embodiments, the biological sample is blood, serum or plasma.

In some embodiments, determining the level of expression includes determining the level of mRNA for dynactin subunit p62.

In some embodiments of the aforementioned methods of diagnosing Alzheimer's Disease, determining the level of expression includes determining the level of protein for dynactin subunit p62.

In some embodiments, determining the level of expression includes contacting said biological sample with antibodies against dynactin subunit p62. Also in the same aspect, determining the level of expression includes an assay selected from the group consisting of immunoassay, mass spectrometry, immuno-mass spectrometry and suspension bead array. Further in the same aspect, the immunoassay is an enzyme linked immunosorbent assay (ELISA). Additionally in the same aspect, the mass spectrometry comprises tandem mass spectroscopy (MSMS).

In another aspect, a kit for detecting Alzheimer's Disease in a subject is provided. In some embodiments, a kit includes, for example, an agent that specifically detects dynactin subunit p62 and instructions for using the kit components to determine the level of expression of dynactin subunit p62. In one aspect, the agent that specifically detects dynactin subunit p62 is an antibody.

Several embodiments relate to a method of screening for a therapeutic agent useful in the prophylaxis or treatment of AD comprising providing a candidate agent to a AD subject, assaying the levels dynactin p62 in the brain of the subject, and comparing the dynactin p62 levels in the brain of the treated subject with an untreated control, wherein an increase in dynactin p62 levels identifies the candidate agent as a therapeutic agent. Several embodiments relate to a method of screening for a therapeutic agent useful in the prophylaxis or treatment of AD comprising providing a candidate agent to a subject having one or more characteristics of AD, assaying synaptic vesicle copper levels in the brain of the subject, and comparing synaptic vesicle copper levels in the brain of the treated subject with an untreated control, wherein an increase in synaptic vesicle copper levels identifies the candidate agent as a therapeutic agent. In some embodiments, the subject may be a transgenic mouse model of AD. In some embodiments, the candidate agent may be provided as a single dose. In some embodiments, the candidate agent may be provided as a series of doses administered every 30 minutes, hour, two hours, four hours, eight hours, 12 hours, 18 hours, 24 hours, week, two weeks, or month. In some embodiments, the candidate agent may be provided continuously. In some embodiments, a period of time (e.g., one minute, 10 minutes, 30 minutes, one hour, two hours, four hours, eight hours, 12 hours, 18 hours, 24 hours, two days, three days, 1 week, two weeks, 1 month, 2 months, three months, 6 months or 1 year) elapses before dynactin p62 or synaptic vesicle copper levels are measured.

Several embodiments relate to an in vitro method for screening for a therapeutic agent useful in the prophylaxis or treatment of AD, comprising establishing a baseline level of dynactin p62, contacting a cultured neuronal cell or tissue with a candidate agent, measuring the dynactin p62 level in the treated neuronal cell or tissue, comparing the dynactin p62 level after treatment to the baseline, and identifying an agent which increases dynactin p62 levels as a therapeutic agent. Several embodiments relate to an in vitro method for screening for a therapeutic agent useful in the prophylaxis or treatment of AD, comprising establishing a baseline level of synaptic vesicle copper, contacting a cultured neuronal cell or tissue with a candidate agent, measuring the synaptic vesicle copper level in the treated neuronal cell or tissue, comparing the synaptic vesicle copper level after treatment to the baseline, and identifying an agent which increases synaptic vesicle copper levels as a therapeutic agent. In some embodiments, the neuronal cell or tissue may be derived from a human AD patient without CAA. In some embodiments, the neuronal cell or tissue may be derived from an animal model of AD. In some embodiments, the subject may be a transgenic mouse model of AD. In some embodiments, the neuronal cells or tissue can be exposed to a candidate agent for a period of time (e.g., one minute, 10 minutes, 30 minutes, one hour, two hours, four hours, eight hours, 12 hours, 18 hours, 24 hours, two days, three days, 1 week, two weeks, 1 month, 2 months, three months or longer), after which the candidate agent is removed, and the cells are cultured for an additional period of time (e.g., one minute, 10 minutes, 30 minutes, one hour, two hours, four hours, eight hours, 12 hours, 18 hours, 24 hours, two days, three days, 1 week, two weeks, 1 month, 2 months, three months or longer) and dynactin p62 or synaptic vesicle copper levels are measured.

Several embodiments relate to a method of indentifying factors that prevent or slow the onset of AD characteristics, by providing a candidate agent to a subject prior to onset of AD, assaying the levels dynactin p62 in the brain of the subject at a later time point, and comparing the dynactin p62 levels in the brain of the treated subject with an untreated control, wherein increased dynactin p62 levels in the treated subject is indicative of prophylaxis. Several embodiments relate to a method of indentifying factors that prevent or slow the onset of AD characteristics, by providing a candidate agent to a subject prior to onset of AD, assaying the levels synaptic vesicle copper in the brain of the subject at a later time point, and comparing the synaptic vesicle copper levels in the brain of the treated subject with an untreated control, wherein increased synaptic vesicle copper levels in the treated subject is indicative of prophylaxis. In some embodiments, the subject may be a transgenic mouse model of AD.

BRIEF DESCRIPTION OF THE DRAWINGS

Aspects of the disclosure will be readily apparent from the description below and the appended drawings, which are meant to illustrate and not to limit the disclosure, and in which.

DETAILED DESCRIPTION OF CERTAIN INVENTIVE EMBODIMENTS

Figure 2A:
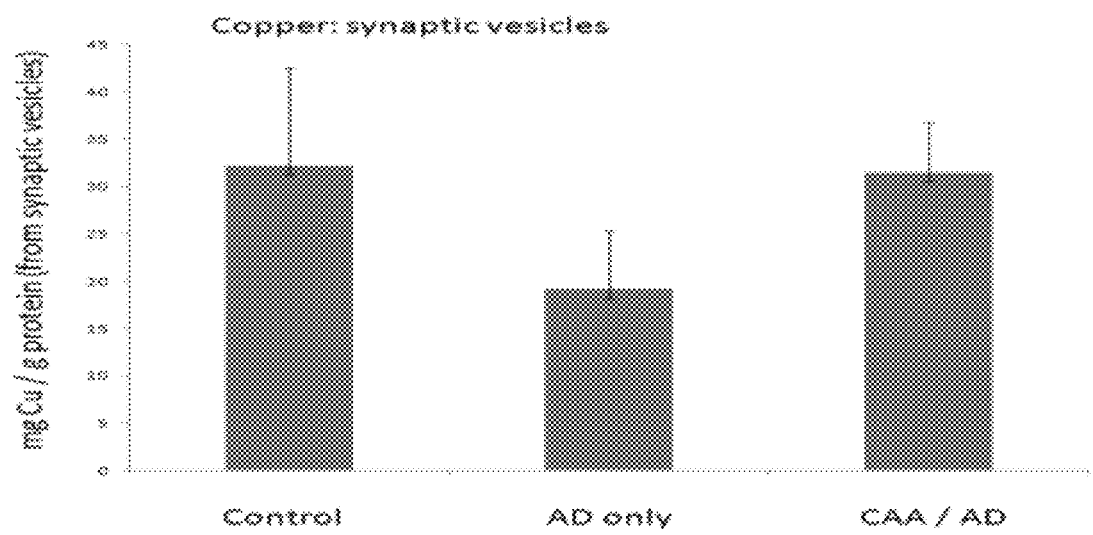
FIG. 2 illustrates copper levels in enriched synaptic vesicles isolated from brain homogenates of control subjects and Alzheimer's Disease (AD) subjects, with or without cerebral amyloid angiopathy (CAA). Copper levels in enriched synaptic vesicle preparation are significantly reduced in AD cases without significant CAA involvement (FIG. 2A). CS3 staining of monovalent copper (FIG. 2B) demonstrates accumulation of copper in the axons in brain from cases with AD pathology without significant CAA. Copper in synaptic vesicles is primarily divalent and therefore not visible in the histological images. These findings suggest there may be an abnormality in axonal trafficking of copper.
Figure 2B:
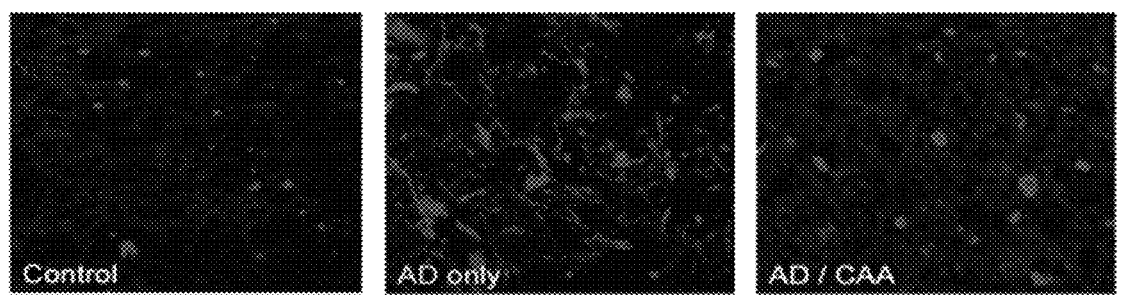

Under normal conditions, copper is concentrated within synaptic vesicles and released into the synaptic cleft with neurotransmitters, modulating and protecting the synapse from NMDA excitotoxicity. Copper content is depleted in Alzheimer's disease neocortex by 40% compared to controls. See Schrag M, Mueller C, Oyoyo U, Smith M A, Kirsch W M. Iron, zinc and copper in the Alzheimer's disease brain: a quantitative meta-analysis. Some insight on the influence of citation bias on scientific opinion. Prog Neurobiol. 2011; 94(3):296-306, incorporated herein by reference. Examination of brain tissue of Alzheimer's Disease cases with negligible (AD) or excessive cerebral amyloid angiopathy (CAA/AD) revealed that copper is significantly depleted from the synaptic vesicles of AD brains compared to control and CAA/AD brains. See FIG. 2A and Example 1. When localization of copper was examined by imaging frozen brain sections, a remarkable axonal redistribution of copper was observed in AD cases but not in CAA/AD cases. See FIG. 2B and Example 1. The intense axonal and cell body staining pattern for Cu(I) observed in AD brain tissue suggests that axonal transport is defective.

Figure 1:
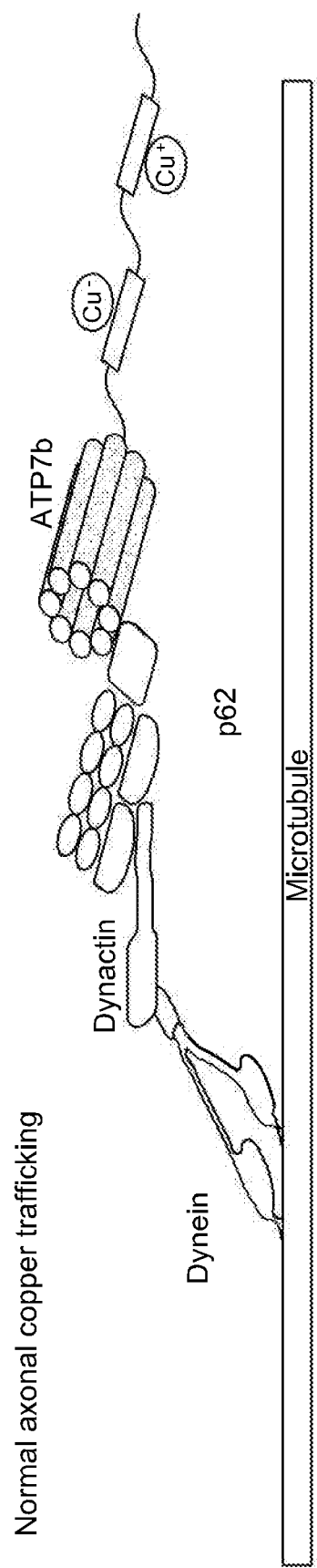
FIG. 1 depicts a model of normal axonal copper trafficking. Monovalent copper (Cu(I)) interacts with CXXC motifs of P type ATPases (ATP7A,7B). Both retrograde and multigrade Cu(I) axonal trafficking requires an interaction between the Cu(I) containing P-type ATPase ATP7B, the dynactin p62 subunit, and dynein/Kinesin II.

Analysis of dynactin p62 localization in histologically in frozen sections of temporal lobe tissue revealed that dynactin p62 and ATP7B, a major copper chaperone, co-localize in normal and AD temporal lobe tissue. The p62 subunit of dynactin, which was found to be increased in the plasma and decreased in the brain of AD (see FIG. 3B) acts as a linker for ATP7B to the axonal motor proteins dynein and kinesin II for axonal transport. FIG. 1.

Embodiments disclosed herein generally relate to diagnostic methods for the detection of neurological conditions. Several embodiments relate to detecting a level of expression of dynactin subunit p62 and comparing the level to a predetermined level indicative of a subject not having a neurological condition, wherein a difference in the detected level compared to the predetermined level indicates a greater likelihood of the neurological condition.

The terms "individual," "host," "subject" and "patient" are used interchangeably herein, and refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein, the terms "ameliorating," "treating," "treatment," "therapeutic," or "therapy" do not necessarily mean total cure or abolition of the disease or condition. Any alleviation of any undesired signs or symptoms of a disease or condition, to any extent, can be considered amelioration, treatment and/or therapy. Furthermore, treatment may include acts that may worsen the patient's overall feeling of well-being or appearance.

The term "nucleic acids", as used herein, may be DNA or RNA. Nucleic acids may also include modified nucleotides that permit correct read through by a polymerase and do not alter expression of a polypeptide encoded by that nucleic acid. The terms "nucleic acid" and "oligonucleotide" are used interchangeably to refer to a molecule comprising multiple nucleotides. As used herein, the terms refer to oligoribonucleotides as well as oligodeoxyribonucleotides. The terms shall also include polynucleosides (for example, a polynucleotide minus the phosphate) and any other organic base containing polymer. Nucleic acids include vectors, for example, plasmids, as well as oligonucleotides. Nucleic acid molecules can be obtained from existing nucleic acid sources, but are preferably synthetic (for example, produced by oligonucleotide synthesis).

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, for example, by the addition of carbohydrate residues to form glycoproteins. The terms "polypeptide," "peptide" and "protein" include glycoproteins, as well as non-glycoproteins. Polypeptide products can be biochemically synthesized such as by employing standard solid phase techniques. Such methods include but are not limited to exclusive solid phase synthesis, partial solid phase synthesis methods, fragment condensation, classical solution synthesis. These methods are preferably used when the peptide is relatively short (for example, 10 kDa) and/or when it cannot be produced by recombinant techniques (for example, not encoded by a nucleic acid sequence) and therefore involves different chemistry. Solid phase polypeptide synthesis procedures are well known in the art and further described by John Morrow Stewart and Janis Dillaha Young, Solid Phase Peptide Syntheses (2nd Ed., Pierce Chemical Company, 1984). Synthetic polypeptides can optionally be purified by preparative high performance liquid chromatography [Creighton T. (1983) Proteins, structures and molecular principles. WH Freeman and Co. N.Y.], after which their composition can be confirmed via amino acid sequencing. In cases where large amounts of a polypeptide are desired, it can be generated using recombinant techniques such as described by Bitter et al., (1987) Methods in Enzymol. 153:516-544, Studier, et al. (1990) Methods in Enzymol. 185:60-89, Brisson et al. (1984) Nature 310:511-514, Takamatsu et al. (1987) EMBO J. 6:307-311, Coruzzi, et al. (1984) EMBO J. 3:1671-1680 and Brogli, et al., (1984) Science 224:838-843, Gurley, et al. (1986) Mol. Cell. Biol. 6:559-565 and Weissbach & Weissbach, 1988, Methods for Plant Molecular Biology, Academic Press, NY, Section VIII, pp 421-463.

As used herein, a result is considered "significant" if the p value for the result is less than 0.05. In certain preferred embodiments, significant results have a p value less than 0.01, and even more preferably less than 0.001.

Detection Methods

Some embodiments disclosed herein relate to diagnostic and prognostic methods for the detection of a neurological condition and/or monitoring the progression of a neurological condition. As used herein the phrase "diagnostic" means identifying the presence of or nature of a neurological condition. The detection of the level of expression of one or more biomarkers provides a means of diagnosing the neurological condition. Such detection methods may be used, for example, for early diagnosis of the condition, to determine whether a subject is predisposed to a neurological condition, to monitor the progress of the condition or the progress of treatment protocols, to assess the severity of the neurological condition, to forecast an outcome of a neurological conditions and/or prospects of recovery, to determine whether a subject is predisposed to a particular subgroup of a neurological condition, to diagnose a particular subgroup of a neurological condition, or to aid in the determination of a suitable treatment for a subject. The detection can occur in vitro, in situ, ex vivo, in silico, or in vivo.

The term "detect" or "measure" refers to identifying the presence, absence, amount, or level of the object to be detected (for example, a biomarker). As used herein, the term "level" refers to expression levels of RNA and/or protein or to DNA copy number of a biomarker. Typically, the level of the marker in a biological sample obtained from the subject is different (for example, increased or decreased) from a predetermined level (for example, the level of the same variant in a similar sample obtained from a healthy individual.

As used herein, "predetermined level" refers to the level of expression of a biomarker in a control sample (for example, a biological sample from a subject without a neurological condition). In some embodiments, the neurological condition can be diagnosed by assessing whether the biomarker expression varies from a predetermined level. For instance, the difference may be greater than, less than, equal to, or any number in between about 5%, 10%, 15%, 20%, 25%, 30%, 35%, 40%, 45%, 50%, 55%, 60%, 65%, 70%, 75%, 80%, 85%, 90%, 95%, 100%, 110%, 125%, 150%, 175%, 200%, 250%, 300%, 350%, 400%, 450%, 500%, 550%, 600%, 650%, 700%, 750%, 800%, 850%, 900%, 950%, 1,000%, 5,000%, 10,000% or 100,000%. The predetermined level can be determined from a control. A control can be a sample or its equivalent from a normal patient or from a patient in a known disease state. For instance, the control can be from a patient with AD, MCI or brain microhemorrhages. The control can also be a standard or known amount of a reference biomarker (for example, protein or mRNA).

The term "about" or "approximately" means within an acceptable error range for the particular value as determined by one of ordinary skill in the art, which will depend in part on how the value is measured or determined, for example, the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

In some embodiments, labels can be used to aid in detection. For example, moieties (for example, antibodies) used to detect a biomarker can be labeled. The term "label" includes any moiety or item detectable by spectroscopic, photo chemical, biochemical, immunochemical, or chemical means. For example, useful labels include fluorescent dyes, radionuclides, phosphors, electron-dense reagents, enzymes, enzyme products (for example, chromagens catalytically processed by horseradish peroxidase or alkaline phosphatase commonly used in an ELISA or immunocytochemistry), biotin-avidin and streptavadin/polymer systems, dioxigenin, colloidal dye substances, fluorochromes, reducing substances, latexes, metals, particulates, dansyl lysine, antibodies, protein A, protein G, chromophores, haptens, and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label can be incorporated in or attached to a primer or probe either covalently, or through ionic, van der Waals or hydrogen bonds, for example, incorporation of radioactive nucleotides, or biotinylated nucleotides that are recognized by avidin/streptavadin. The label may be directly or indirectly detectable. Indirect detection can involve the binding of a second label to the first label, directly or indirectly. For example, the label can be the ligand of a binding partner, such as biotin, which is a binding partner for avidin/streptavadin, or a nucleotide sequence, which is the binding partner for a complementary sequence, to which it can specifically hybridize. The binding partner may itself be directly detectable, for example, an antibody may be itself labeled with fluorescent molecules and/or enzymes (for example, HRP or alkaline phosphatase). The binding partner also may be indirectly detectable, for example, a nucleic acid having a complementary nucleotide sequence can be a part of a branched DNA molecule that is in turn detectable through hybridization with other labeled nucleic acid molecules (see, for example, P. D. Fahrlander and A. Klausner, Bio/Technology 6:1165 (1988)). Quantitation of the signal is achieved by, for example, scintillation counting, densitometry, flow cytometry and/or microscopical analysis with computer-algorithm assisted software(s).

Examples of detectable labels, optionally and preferably for use with immunoassays, include but are not limited to magnetic beads, fluorescent dyes, radiolabels, enzymes, chromagens catalytically processed by enzymes (for example, horseradish peroxide (HRP), alkaline phosphatase and others commonly used in an ELISA and immunocytochemisry), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Visualization of enzymes, (for example, HRP or alkaline phosphatase), can be achieved by means of using the enzymatic activity of the enzyme, for example, the oxidative-catalytic enzymatic activity of HRP or Alkaline phosphatase, to process and precipitate a substrate-chromogen. The final reaction product may be soluble in buffer or ethanol and may require stabilization to prevent fading. Chromogens that can be used include, but are not limited to 3,3'-diaminobenzidine tetrahydrochloride (DAB), Betazoid DAB, Cardassian DAB, 3,3',5,5'-tetramethylbenzidine (TMB), benzidine dihydrochloride (BDHC) and p-phenylenediamine dihydrochloride with pyrocatechol (PPD-PC), 4-chloro-1-naphthol (4C1N), 3-amino-9-ethylcarbazole (AEC) and o-phenylenediamine (OPD), DAB-NI (Vector Laboratories), VECTOR® VIP (Vector Laboratories), VECTOR® SG (Vector Laboratories), VECTOR® RED (Vector Laboratories), VECTOR® BLACK (Vector Laboratories), VECTOR® BLUE (Vector Laboratories), BCIP/NBT (Vector Laboratories), Glucose oxidase NBT (Vector Laboratories), Glucose oxidase TNBT (Vector Laboratories), and Glucose oxidase INT (Vector Laboratories), Bajoran Purple, Romulin AEC, Ferangi Blue and Vulcan Fast Red (Biocare Medical Inc.). Some chromogens (for example, Bajoran Purple and VECTOR® RED) may also be used in double and triple stain procedures, nitrocellulose blots, and can be viewed by both bright- and darkfield microscopy. The visualization of the reaction product can be further improved by intensification with metal salts. At the light microscopic level, this intensification can enable color differentiation between distinct markers (see, for example, van der Want et al., Tract-tracing in the nervous system of vertebrates using horseradish peroxidase and its conjugates: tracers, chromogens and stabilization for light and electron microscopy. *Brain Res Brain Res Protoc.* 1997 August 1(3):269-79, which is hereby incorporated by reference for the subject mater for which it is cited and in its entirety). In addition, the amounts of these precipitates can be semi-automatically or automatically quantified by algorithm based software (for example, Aperio Technology Inc, Vista, Calif.). Visualization can be achieved by using combinations of detectable labels in embodiments disclosed herein. For example, HRP can be used with alkaline phosphatase and visualized by microscopy (for example, bright- or dark-field microscopy) to differentiate between two or more distinct markers.

Examples of fluorescent dyes include, but are not limited to, 7-Amino-actinomycin D, Acridine orange, Acridine yellow, Alexa Fluor dyes (Molecular Probes), Auramine O, Auramine-rhodamine stain, Benzanthrone, 9,10-Bis(phenylethynyl)anthracene, 5,12-Bis(phenylethynyl)naphthacene, CFDA-SE, CFSE, Calcein, Carboxyfluorescein, 1-Chloro-9,10-bis(phenylethynyl)anthracene, 2-Chloro-9,10-bis(phenylethynyl)anthracene, Coumarin, Cyanine, DAPI, Dark quencher, Dioc6, DyLight Fluor dyes (Thermo Fisher Scientific), Ethidium bromide, Fluorescein, Fura-2, Fura-2-acetoxymethyl ester, Green fluorescent protein and derivatives, Hilyte Fluor dyes (AnaSpec), Hoechst stain, Indian yellow, Luciferin, Perylene, Phycobilin, Phycoerythrin, Phycoerythrobilin, Propidium iodide, Pyranine, Rhodamine, RiboGreen, Rubrene, Ruthenium(II) tris(bathophenanthroline disulfonate), SYBR Green, Stilbene, Sulforhodamine 101, TSQ, Texas Red, Umbelliferone, and Yellow fluorescent protein.

Examples of phsosphors include, but are not limited to Phosphor, Anthracene, Barium fluoride, Bismuth germanate, Cadmium sulfide, Cadmium tungstate, Gadolinium oxysulfide, Lanthanum bromide, Polyvinyl toluene, Scheelite, Sodium iodide, Stilbene, Strontium aluminate, Yttrium aluminium garnet, Zinc selenide, Zinc sulfide Examples of radionuclides include, but are not limited to, $^{32}$P, $^{33}$P, $^{43}$K, $^{47}$Sc, $^{52}$Fe, $^{52}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81}$MKr, $^{87}$MSr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi, and $^{213}$Bi. Antibodies can be radiolabeled, for example, by the Iodogen method according to established methods.

A label may be chemically coupled directly to an antibody (for example, without a linking group) through an amino group, a sulfhydryl group, a hydroxyl group, or a carboxyl group. In some embodiments, a label can be attached to an antibody via a linking group. The linking group can be any biocompatible linking group, where "biocompatible" indicates that the compound or group can be non-toxic and may be utilized in vitro or in vivo without causing injury, sickness, disease, or death. The label can be bonded to the linking group, for example, via an ether bond, an ester bond, a thiol bond or an amide bond. Suitable biocompatible linking groups include, but are not limited to, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl butanoate (SBA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine.

The protein biomarkers (including, for example, dynactin subunit p62) can be detected using a variety of methods known in the art. Some embodiments disclosed herein relate to methods of detecting a biomarker that is immunological in nature. "Immunological" refers to the use of antibodies (for example, polyclonal or monoclonal antibodies) specific for a biomarker. The phrase "specific for a biomarker," "specifically binds to a biomarker," or "specifically detects a biomarker" refers to, for example, antibodies that recognize the biomarker while not substantially cross-reacting with control samples containing other proteins. Antibodies specific for a biomarker include, but are not limited to, commercially available antibodies (for example, antibodies commercially available that recognize dynactin subunit p62) and those antibodies that can be produced by methods disclosed herein and by methods known in the art. Antibodies specific for the biomarkers can be produced readily using well known methods in the art. (See J. Sambrook, E. F. Fritsch and T. Maniatis, *Molecular Cloning, a Laboratory Manual*, second edition, Cold Spring Harbor Laboratory Press, pp. 18.7-18.18, 1989) For example, the biomarkers can be prepared readily using an automated peptide synthesizer. Next, injection of an immunogen (for example, a biomarker), such as (peptide)$_n$-KLH (n=1-30) in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Fine specificity of generated antibodies can be detected by using peptide fragments of the original immunogen.

The term "antibody" includes immunoglobulin molecules and immunologically active determinants of immunoglobulin molecules, for example, molecules that contain an antigen binding site which specifically binds (for example, immunoreacts with) an antigen. Structurally, the simplest naturally occurring antibody (for example, IgG) comprises four polypeptide chains, two copies of a heavy (H) chain and two of a light (L) chain, all covalently linked by disulfide bonds. Specificity of binding in the large and diverse set of antibodies is found in the variable (V) determinant of the H and L chains; regions of the molecules that are primarily structural are constant (C) in this set. The term "antibody" includes, but is not limited to, polyclonal antibodies, monoclonal antibodies, whole immunoglobulins, and antigen binding fragments of the immunoglobulin.

The binding sites of the proteins that comprise an antibody, for example, the antigen-binding functions of the antibody, are localized by analysis of fragments of a naturally-occurring antibody. Thus, antigen-binding fragments are also intended to be designated by the term "antibody." Examples of binding fragments encompassed within the term antibody include: a Fab fragment consisting of the VL, VH, CL and CH1 domains; an F$_c$ fragment consisting of the VH and CH1 domains; an F$_v$ fragment consisting of the V$_L$, and V$_H$ domains of a single arm of an antibody; a dAb fragment (Ward et al., 1989 Nature 341:544-546) consisting of a VH domain; an isolated complementarity determining region; and an F(ab')$_2$ fragment, a bivalent fragment comprising two Fab' fragments linked by a disulfide bridge at the hinge region. These antibody fragments are obtained using conventional techniques well-known to those with skill in the art, and the fragments are screened for utility in the same manner as are intact antibodies. The term "antibody" is further intended to include bispecific and chimeric molecules having at least one antigen binding determinant derived from an antibody molecule, as well as single chain (scFv) antibodies. The term "single-chain Fv," also abbreviated as "sFv" or "scFv," refers to antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

Quantification assays for a biomarker and detection of a biomarker can use binding molecules specific for the biomarker other than antibodies, including but not limited to, affibodies, aptamers or other specific binding molecules known in the art.

Examples of acceptable immunoassays include, for example, ELISA, radioimmunoassay, immunofluorescent assay, "sandwich" immunoassay, Western blot, immunoprecipitation assay and immunoelectrophoresis assays. In other aspects, microbeads, arrays, microarrays, etc. can be used in detecting the LMW peptides. Examples of acceptable assays include, but are not limited to, a suspension bead assay (Schwenk, et al., "Determination of binding specificities in highly multiplexed bead-based assays for antibody proteomics," *Mol. Cell Proteomics,* 6(1): 125-132 (2007)), an antibody microarray (Borrebaeck et al., "High-throughput proteomics using antibody microarrays: an update," *Expert Rev. Mol. Diagn.* 7(5): 673-686 (2007)), an aptamer array (Walter, et al., "High-throughput protein arrays: prospects for molecular diagnostics," *Trends Mol. Med.* 8(6): 250-253 (2002)), an affybody array (Renberg, et al., "Affibody molecules in protein capture microarrays: evaluation of multi-domain ligands and different detection formats," *J. Proteome Res.* 6(1): 171-179 (2007)), and a reverse phase array (VanMeter, et al., "Reverse-phase protein microarrays: application to biomarker discovery and translational medicine," *Expert Rev. Mol. Diagn.* 7(5): 625-633 (2007)). All of these publications are incorporated herein by reference for the subject matter for which they are cited and in their entireties.

In other embodiments, the biomarkers can be detected using mass spectrometry (MS). One example of this approach is tandem mass spectrometry (MS/MS), which involves multiple steps of mass selection or analysis, usually separated by some form of fragmentation. Most such assays use electrospray ionization followed by two stages of mass selection: a first stage (MS1) selecting the mass of the intact analyte (parent ion) and, after fragmentation of the parent by collision with gas atoms, a second stage (MS2) selecting a specific fragment of the parent, collectively generating a selected reaction monitoring assay. In one embodiment, collision-induced dissociation is used to generate a set of fragments from a specific peptide ion. The fragmentation process primarily gives rise to cleavage products that break along peptide bonds. Because of the simplicity in fragmentation, the observed fragment masses can be compared to a database of predicted masses for known peptide sequences. A number of different algorithmic approaches have been described to identify peptides and proteins from tandem mass spectrometry (MS/MS) data, including peptide fragment fingerprinting (SEQUEST, MASCOT, OMSSA and X!Tandem), peptide de novo sequencing (PEAKS, LuteFisk and Sherenga) and sequence tag based searching (SPIDER, GutenTAG).

In some embodiments, multiple reaction monitoring (MRM) can be used to identify the biomarkers in patient samples. This technique applies the MS/MS approach to, for example, tryptic digests of the input sample, followed by selected ion partitioning and sampling using MS to make the analyte selection more objective and discrete by following the exact m/z ion of the tryptic fragment that represents the analyte. Such an approach can be performed in multiplex so that multiple ions can be measured at once, providing an antibody-free method for analyte measurement. See, for example, Andersen et al., *Molecular & Cellular Proteomics,* 5.4: 573-588 (2006); Whiteaker, et al., *J. Proteome Res.* 6(10): 3962-75 (2007). Both publications are incorporated herein by reference for the subject matter for which they were cited and in their entireties.

In further embodiments, the biomarkers can be detected using nanoflow reverse-phase liquid chromatography-tandem mass spectrometry. See, for example, Domon B, Aebersold R. *Science,* 312(5771):212-7(2006), which is incorporated herein by reference for the subject matter for which it is cited and in its entirety. Using this approach, practitioners obtain peptide fragments, usually by trypsin digest, and generate mass spectrograms of the fragments, which are then compared to a database, such as SEQUEST, for protein identification.

In other aspects, the biomarkers can be detected using immuno-mass spectrometry. See, for example, Liotta L., et al. J. Clin. Invest., 116(1):26-30 (2006) and Nedelkov, Expert Rev. Proteomics, 3(6): 631-640 (2006), which are incorporated herein by reference. Immuno-mass spectrometry provides a means for rapidly determining the exact size and identity of a peptide biomarker isoform present within a patient sample. When developed as a high throughput diagnostic assay, a drop of patient's blood, serum or plasma can be applied to a high density matrix of microcolumns or microwells filled with a composite substratum containing immobilized polyclonal antibodies, directed against the peptide marker. All isoforms of the peptide that contain the epitope are captured. The captured population of analytes including the analyte fragments are eluted and analyzed directly by a mass spectrometer such as MALDI-TOF MS. The presence of the specific peptide biomarker at its exact mass/charge (m/z) location can be used as a diagnostic test result. The analysis can be performed rapidly by simple software that determines if a series of ion peaks are present at defined m/z locations.

In yet more embodiments, the biomarkers can be detected using standard immunoassay-based approaches whereby fragment specific antibodies are used to measure and record the presence of the diagnostic fragments. See, for example, Naya, et al. "Evaluation of precursor prostate-specific antigen isoform ratios in the detection of prostate cancer." *Urol Oncol.* 23(1):16-21 (2005). Moreover, additional immunoassays are well known to one skilled in the field, such as ELISA (Maeda et al., "Blood tests for asbestos-related mesothelioma," *Oncology* 71: 26-31 (2006)), microfluidic ELISA (Lee et al., "Microfluidic enzyme-linked immunosorbent assay technology," *Adv. Clin. Chem.* 42: 255-259 (2006)), nanocantilever immunoassay (Kurosawa et al., "Quartz crystal microbalance immunosensors for environmental monitoring," *Biosens Bioelectron,* 22(4): 473-481 (2006)), and plasmon resonance immunoassay (Nedelkov, "Development of surface Plasmon resonance mass spectrometry array platform," *Anal. Chem.* 79(15): 5987-5990 (2007)). All publications are incorporated herein by reference for the subject matter for which they are cited and in their entireties.

In further embodiments, the biomarkers can be detected using electrochemical approaches. See, for example, Lin et al., Anal. Sci. 23(9): 1059-1063 (2007)), which is hereby incorporated by reference for the subject mater for which it is cited and in its entirety.

In some embodiments, the expression of a biomarker can be detected by measuring levels of mRNA encoding a protein biomarker. Any technique known in the art can be used to detect mRNA levels of biomarkers. Those of skill in the art are well acquainted with methods of mRNA detection, for example, via the use of complementary hybridizing primers (for example, labeled with radioactivity or fluorescent dyes) with or without polymerase chain reaction (PCR) amplification of the detected products, followed by visualization of the detected mRNA via, for example, electrophoresis (for example, gel or capillary); by mass spectroscopy; etc. The level of mRNA may also be measured, for example, using ethidium bromide staining of a standard RNA gel, Northern blotting, primer extension, or a nuclease protection assay. Other means of detecting the expression profile of mRNA encoding a protein biomarker include, but are not limited to, PCR-based methods (for example, quantitative real time PCR), microarray based methods, and ribonuclease protection assays (RPA).

Additional means of detecting the expression of a biomarker include, but are not limited to, detecting the level of promoter modification (for example, methylation) and detecting the level of histone modification. For example, promoter methylation has been shown to correlate with mRNA expression (see, for example, Lindsey, et al. 2007 Jul. 16; 97(2):267-74, which is hereby incorporated by reference for the subject matter for which it is cited and in its entirety).

Further means of detecting the expression of a biomarker include, but are not limited to, determining the level DNA encoding the biomarker. These methods include, but are not limited to, various approaches for DNA sequencing (to find, for example, mutations or deletions) and other approaches known in the art.

Neurological Conditions

The neurological condition or disease being detected according to the methods described herein can be, for example, Alzheimer's disease (AD), mild cognitive impairment (MCI), stable mild cognitive impairment (stable MCI), mild AD, vascular dementia (VD), angiopathy black holes, cerebral amyloid angiopathy (CAA) and/or brain microhemorrhages. The neurological condition or disease being detected according to the methods described herein can also be a subgroup of Alzheimer's disease such as AD without CAA. Unless otherwise indicated, the conditions and activities noted herein refer to the commonly accepted definitions thereof. For instance, as described in more detail in the Examples, cognitive impairment is defined according to the Mayo Clinic criteria.

Levels of biomarkers described herein can be useful in detecting a neurological condition during its early stages, such as while the condition is still associated with MCI or mild AD or for detecting brain vasculopathy, such as brain microhemorrhages. Conditions can be classified according to various criteria and/or cognitive tests known in the art (See, for example, Petersen R C J Intern Med (2004) 256:183-194; Petersen et al. (1999) Arch Neurol 56:303-308; Reisberg B. (2007) Int. Psychogeriatr. 19:421-456). Cognitive tests include, for example, Logical Memory I and II, Wisconsin Card Sorting Test, Trail Making Test A and B, Boston Naming Test, Draw-A Clock, Geriatric Depression Scale, Word Fluency (Phonemic and Semantic) and videotaped Global Clinical Dementia Rating (CDR) with informant. Mild cognitive impairment (MCI) cases can fulfill the Mayo Clinic criteria for classification as MCI-multiple domain impairment (MCI-MCDI) with the following characteristics: i) A memory complaint confirmed by either corrected Logical Memory testing or reports of the informant and a Clinical Dementia Rating (CDR)=0.5. ii) Normal activities of daily living. iii) Normal general cognitive function. iv) Abnormal memory for age as measured by standard scores and education. v) A global CDR of 0.5 and no dementia. vi) No history of significant vascular problems, insulin-requiring diabetes, or uncontrolled hypertension. Meanwhile, stable mild cognitive impairment (stable MCI) can be classified based on a sum of boxes=0.5-3.5 on several evaluations, CDR logical memory impairment with logical memory impairment on at least one evaluation, and/or neuropsychological testing in MCI range inconsistently and clinical judgment. Progression to dementia (mild AD) can be classified by a sum of CDR boxes of 3.5 or more, NINCDS-ARDRDA criteria, neuropsychological tests congruent with CDR, a Logical Memory raw score low to zero and/or clinical judgment. The parameters described above can be useful in identifying subjects at risk of a neurological condition.

Levels of biomarkers described herein can be useful in detecting a subgroup of a neurological condition, such as the subgroup of Alzheimer's Disease without cerebral amyloid angiopathy (CAA) or evidence of microbleeds. Cerebral amyloid angiopathy (CAA), also known as congophilic angiopathy or cerebrovascular amyloidosis, is a disease of small blood vessels in the brain in which deposits of amyloid protein in the vessel walls may lead to stroke, brain hemorrhage, or dementia. In Alzheimer's disease, CAA is more common than in the general population, and may occur in more than 80% of patients over age 60. CAA is characterized by small blood vessel bleeding. This bleeding is caused when the amyloid protein A Beta 40 is targeted to the small blood vessel wall, where it triggers oxidative stress that opens the vessel wall and causes microhemorrhages (MH).

Biological Samples

In some embodiments, the biomarkers are harvested from a biological sample prior to their detection. Numerous well known tissue or fluid collection methods can be utilized to collect the biological sample from the subject in order to determine the level of DNA, RNA and/or protein or fragment thereof of the biomarker(s) of interest in the subject. Biological samples can include, for example, blood, serum, plasma, urine, lymph, tissue and products thereof.

For example, the protein biomarkers can be harvested from a sample using a capture-particle that comprises a molecular sieve portion and an analyte binding portion. Briefly, either the molecular sieve portion or the analyte binding portion or both comprise a cross-linked region having modified porosity, or pore dimensions sufficient to exclude high molecular weight molecules. Examples of such suitable methods are described, for example, in PCT Pub. No. WO/2008/115653, filed Feb. 21, 2008 and PCT Pub. No. WO/2007/038523, filed Sep. 27, 2006, both of which are incorporated herein by reference.

In another embodiment, the protein biomarkers are digested prior to detection, so as to reduce the size of the peptides. Such digestion can be carried out using standard methods well known in the field. Examples of acceptable treatments include, but are not limited to, enzymatic and chemical treatments. Such treatments can yield partial as well as complete digestions. One example of an enzymatic treatment is a trypsin digestion.

Additional methods for obtaining a biological sample include, but are not limited to, fine needle biopsy, needle biopsy, core needle biopsy and surgical biopsy (for example, brain biopsy), lavage, and any known method in the art. Regardless of the procedure employed, once a biopsy/sample is obtained, the biomarker(s) may be identified, the level of the biomarker(s) can be determined, and one or more neurological conditions may be identified and/or monitored and/or treated.

Kits

Some embodiments disclosed herein provide for a kit for use in, for example, the screening, diagnosis, or monitoring the progress of a neurological condition. Such a kit may comprise an agent or binding moiety (for example, an antibody, such as a primary antibody) which specifically detects or binds to a biomarker (for example, dynactin subunit p62) and instructions for use. Such a kit may further comprise a reaction container, various buffers, additional agents or binding moieties, and the like. In some embodiments, the agent or binding moiety is labeled. In one embodiment, the kit further comprises additional agents or binding moieties (for example, secondary antibodies) which binds specifically to the first binding moiety and/or second binding moiety.

In some embodiments, the kit may comprise a reference sample, for example, a negative and/or positive control. In such embodiments, the negative control would be indicative of the absence of the neurological condition and the positive control would be indicative of the neurological condition. A large number of control samples can be assayed to establish the threshold, mode and width of the distribution of a biomarker in a normal biological sample against which test biological samples are compared. These data can be provided to users of the kit.

In one embodiment, the agents or the binding moieties in the kit can be antibodies or fragments thereof which specifically bind to the biomarkers. In these kits, antibodies (for example, primary and/or secondary antibodies) may be provided with means for binding to detectable marker moieties (for example, labels) or substrate surfaces. Alternatively, the kits may include antibodies already bound to marker moieties (for example, labels) or substrates. Antibodies and binding fragments thereof can be, for example, lyophilized or in solution. Additionally, the preparations can contain stabilizers to increase the shelf-life of the kits, for example, bovine serum albumin (BSA). Wherein the antibodies and antigen binding fragments thereof are lyophilized, the kit can contain further preparations of solutions to reconstitute the preparations. Acceptable solutions are well known in the art, for example, PBS. In some embodiments, the antibody is a polyclonal antibody, a monoclonal antibody, a humanized antibody, a chimeric antibody, a recombinant antibody, or fragment thereof.

In some embodiments, the kits can further include the components for an immunohistochemical assay for measuring the biomarker and/or fragments thereof. For example, kits containing antibody bound to multiwell microtiter plates can be provided. The kit may include a standard or multiple standard solutions containing a known concentration of biomarker or other proteins for calibration of the assays. Samples to be tested in this application include, for example, blood, serum, plasma, urine, lymph, tissue and products thereof.

Alternatively, the kits may include immunoassays, such as immunohistochemistry to test subject tissue biopsy sections. The kits may also be used to detect the presence of one or more biomarkers in a biological sample obtained from a subject using immunohistocytochemistry.

The compositions of the kits may be formulated in single or multiple units for either a single test or multiple tests.

The above-mentioned kits may be used for the detection of any neurological condition or subgroup thereof including, without limitation, Alzheimer's disease, mild cognitive impairment, stable mild cognitive impairment, mild Alzheimer's disease, vascular dementia, angiopathy black holes, cerebral amyloid angiopathy, and microhemorrages. The kit may be used to diagnose Alzheimer's disease without CAA or microbleeds. The kit may also be used to determine the severity, aggressiveness or grade of the neurological condition. In some embodiments, kits may also be used for identifying potential candidate therapeutic agents for treating the neurological condition.

Methods Identifying Alzheimer's Disease Therapeutics

Animal models of AD have served as common screening platforms for testing the effectiveness of candidate agents in the treatment or prophylaxis of AD. However the available animal models do not recapitulate the full neuropathological, biochemical, cellular, and morphological changes observed in AD and successful treatments for delaying or halting the progression of the disease have not been established. As described herein, synaptic vesicle copper levels and dynactin p62 levels are reduced in the brains of AD patients with negligible cerebral amyloid angiopathy. Accordingly, synaptic vesicle copper and dynactin p62 levels represent measurable characteristics that can be assessed to evaluate therapeutic treatments for AD.

Several embodiments described herein relate to methods of indentifying factors (such as solvents, small molecule drugs, peptides, polynucleotides, biologics and the like) that affect the characteristics of AD brains. The effectiveness of a candidate agent in the treatment or prophylaxis of AD may be measured by the response of synaptic vesicle copper and dynactin p62 levels to treatment. Factors that increase dynactin p62 levels and normalize axonal copper trafficking in AD brains are suitable as therapeutics to treat, prevent, control, or lessen the severity of AD, or can be used as lead compounds for the development of drugs that have additional desired properties.

The effect of a candidate agent on synaptic vesicle copper and/or dynactin p62 levels may be screened in vivo by administering the candidate agent to an AD model animal or in vitro. Examples of in vitro screening platforms include, but are not limited to hippocampal slices, primary neural cell cultures, hippocampal cell cultures, cultures of embryonic stem cell or pluripotent stem cell derived neurons, and neuronal cell lines. Cells and tissues obtained utilized in in vitro screening methods may be obtained from a human AD patient or from an animal model of AD identified as exhibiting reduced levels of synaptic vesicle copper and/or dynactin p62 as observed in the brains of human AD patients. In some embodiments, the animal model of AD is a transgenic animal. While mice and rats are common model animals, non-human primates, cats, dogs, pigs, goats, cows, or horses may be used.

Dynactin p62 Disruption as a Model of Alzheimer's Disease

Several embodiments relate to neuronal cell lines and transgenic animals in which the function of dynactin p62 is disrupted. Disruption of dynactin p62 function may be achieved by, e.g., mutagenesis, gene "knockout" technology, antisense methodologies, antibody methodologies, ribozyme, or RNAi methodologies. These techniques are familiar to those in the art. Dynactin p62-disrupted neuronal cell lines and transgenic animals may be useful as a model for AD in screening methodologies for identifying therapeutics to treat, prevent, control, or lessen the severity of AD, and to study disease pathology.

Each reference disclosed herein, and throughout the specification, is incorporated by reference for the subject matter for which it is cited and in its entirety. The following examples provide illustrations of some of the embodiments described herein but are not intended to limit the disclosure.

The Examples below describe in further detail the identification of biomarkers for neurological conditions.

EXAMPLE 1

While copper levels in the human brain are considerably lower than either iron or zinc, copper may play a central role in numerous neurodegenerative diseases. Meta-analysis of AD brain iron and zinc levels failed to demonstrate significant changes whereas copper levels, in comparison, were consistently found to be severely depleted throughout the neocortex (p=0.0003). Schrag M, Mueller C, Oyoyo U, Smith M A, Kirsch W M. Iron, zinc and copper in the Alzheimer's disease brain: a quantitative meta-analysis.

Some insight on the influence of citation bias on scientific opinion. Prog Neurobiol. 2011; 94(3):296-306, incorporated herein by reference.

Alterations in copper metabolism can have numerous negative effects. For instance, removing the copper cofactor from super-oxide dismutase reduces its activity, rendering tissues more sensitive to oxidative stress—a mechanism central to ALS pathogenesis (Museth A., et al., "The ALS-associated mutation G93A in human copper-zinc superoxide dismutase selectively destailizes the remote metal binding region. Biochemistry 48:8817-29 (2009), Hayward L, et al., "Decreased metallation and activity in subsets of mutant superoxide dismutases associated with familial amyotrophic later sclerosis." J. Biol Chem 277:15923-31 (2002)); protein disulfide isomerase which is critical for proper protein folding in the endoplasmic reticulum requires a copper cofactor (Narindrasorasak S., et al., "Protein disulfide isomerase, a multifunctional protein chaperone, shows copper-binding activity." Biochem Biophys Res Commun 311: 405-14 (2003)); and genetic abnormalities of copper chaperones (Menkes and Wilson's diseases) result in severe neurological dysfunction and early death (De Bie P., et al., "Molecular pathogenesis of Wilson and Menkes disease: correlation of mutations with molecular defects and disease phenotypes." J Med Genet. 44:673-88 (2007)).

Copper is also bound by prion protein which is associated with Creutfeldt-Jakob disease, alpha-synuclein in Lewy bodies of Parkinsonian brain and by nearly every protein associated with Alzheimer's disease pathology (Wu D, et al., "Copper (II) promotes the formation of soluble neurotoxic PrP oligomers in acidic environment." J Cell Biochem in press. (2010); Wang X, et al., "Copper binding regulates intracellular alpha-synuclein, localization, aggregation and toxicity." J. Neurochem 113:704-14 (2010); Macreadie I, "Copper transport and Alzheimer's disease." Eur Biophys J 37:295-300 (2008)). Beta-secretase requires a copper cofactor, amyloid precursor protein binds and effluxes copper from neurons, and beta-amyloid plaques contain high concentrations of copper in their cores (Dingwall C, "A copper-binding site in the cytoplasmic domain of BACE1 identifies a possible link to metal homeostasis and oxidative stress in Alzheimer's disease." Biochem Soc Trans 35:571-3 (2007); Lovell M, et al., "Copper, iron and zinc in Alzheimer's disease senile plaques. Journal of Neurological Science 158:47-52 (1998)).

Copper is also physiologically concentrated within synaptic vesicles and is released into the synaptic cleft in a burst with neurotransmitters. The copper burst appears to be functionally important, such as for inducing alterations in NMDA receptors and in long-term potentiation (Leiva J., et al., "Copper interaction on the long-term potentiation." Arch Ital Biol 141:149-55 (2003); Schlief M, et al., "Copper homeostasis in the CNS: a novel link between the NMDA receptor and copper homeostasis in the hippocampus." Mol Neurobiol 33:81-90 (2006)).

From brain homogenate, an enriched fraction containing synaptic vesicles was isolated by ultracentrifugation as previously described and copper levels (normalized to protein concentration) were determined by graphite furnace atomic absorption spectroscopy also described previously (Ohsawa K., et al., "New fractionation method of synaptic vesicles in the brain." Proc Japan Acad 51:202-8 ((1975); Schrag M., et al., "The effect of formalin fixation on the levels of brain transition metals in archived samples." Biometals in press. (2010). Copper levels were increased in isolated vesicles 5,000 fold over total brain copper levels (30,000 μg copper/g synaptic protein, vs 6 μg copper/g total brain protein) (Squitti R., et al., "Ceruloplasmin (2D PAGE) pattern and copper content in serum of Alzheimer's disease patients." Biomark Insights 1:205-13 (2006)).

Synaptic vesicles in cases with AD without significant CAA were found to be significantly depleted of copper compared to vesicles from controls and AD cases with severe CAA—n=4 in each group. (FIG. 2A) Histological stains of unfixed brain sections with coppersensor 3 (CS3), a sensitive analogue of the CS1 probe used in previous studies, revealed a remarkable redistribution of copper in AD cases without CAA. (FIG. 2B) The pattern was essentially unchanged between controls and AD/CAA cases, but in AD without CAA an intense axonal staining pattern was present. (FIG. 2B) These findings suggest that there is a defect in axonal transport or in incorporating copper into vesicles in these cases.

Figure 3A:
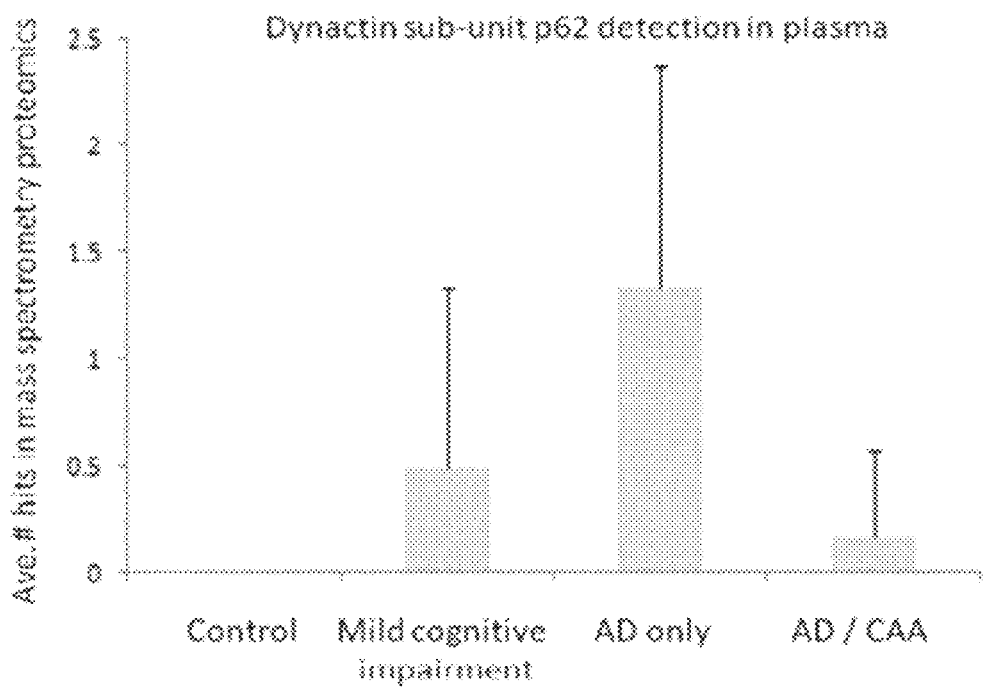
FIG. 3 illustrates levels of expression of the dynactin p62 subunit in plasma collected from neurologically normal subjects, subjects with mild cognitive impairment, AD subjects without radiologic evidence of microbleeds, and AD subjects with multiple microbleeds (FIG. 3A). The p62 subunit of dynactin was found to be significantly elevated in the AD only group and was undetectable in all of the control cases. Western blot analysis of p62 levels in the brain in comparable groups demonstrated the opposite pattern—p62 levels are significantly lowered in the AD only group compared to both controls and AD/CAA groups (FIG. 3B).
Figure 3B:
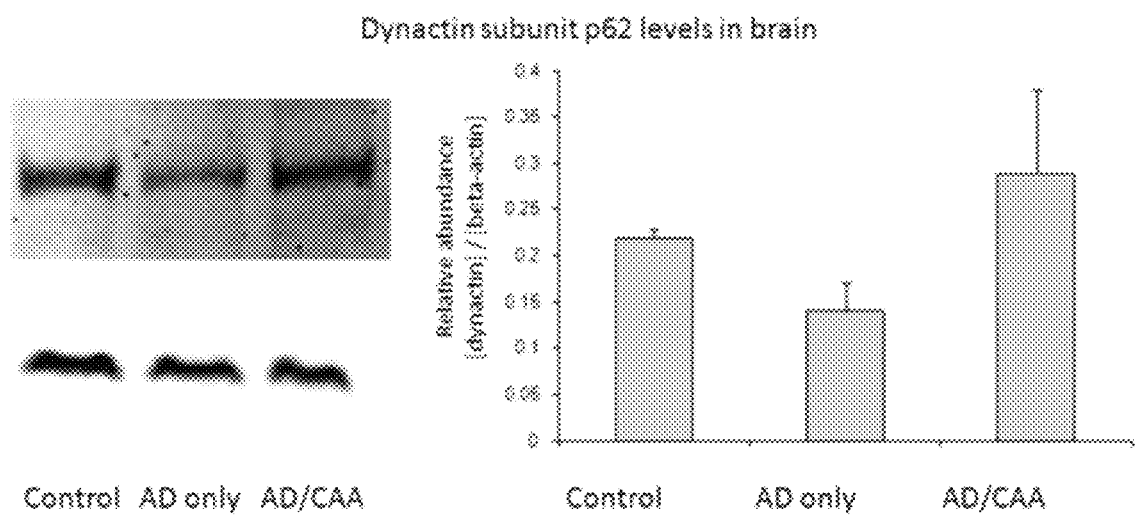

Next, we screened a proteomic database for serum protein changes occurring only in AD without CAA cases. In particular we focused on proteins and protein fragments related to axonal transport. Plasma was collected from four groups of patients—neurologic controls, patients with mild cognitive impairment (MCI), patients with AD without radiologic evidence microbleeding (AD only) and AD patients with multiple microbleeds (AD/CAA)—n=6 in each group. FIGS. 3A and 3B. Samples were analyzed with an orbitrap LC/MS/MS spectrometry (MS) technique as previously described and more than 1500 proteins were identified in the plasma samples (Mueller C, et al., "The heme degradation pathway is a promising serum biomarker source for the early detection of Alzheimer's disease." J Alz Dis 19:1081-91 (2010)).

Dynactin subunit p62 was found to be higher in plasma from AD patients without evidence of CAA (FIG. 3A). Additionally, we assessed the levels of dynactin in the post-mortem brain by Western blot. Dynactin p62 was significantly reduced in the AD only group compared to both controls and AD/CAA, p=0.01 (FIG. 3B). Dynactin is a multisubunit protein complex that directly binds the minus-end-directed microtubule motor dynein and modulates binding of dynein to cell organelles for transport along microtubules. Dynein is targeted to a variety of subcellular structures and requires dynactin for its known functions in organelle and vesicle transport. Dynactin subunit p62 (DCTN4) is a ubiquitously expressed 53 kDa protein that localizes to the cytoplasm and centrosomes. Dynactin also consists of other subunits including DCTN1 (p150Glued), DCTN2/dynamitin, DCTN3/p22/p24, Arp1/centractin, CapZ, Actr10/Arp11, DCTN5/p25, and DCTN6/p27. Confocal microscopy revealed that dynactin p62 and ATP7B co-localize in normal and AD human temporal lobe tissue. The p62 subunit of dynactin, which is increased in the plasma and decreased in the brain of AD without CAA cases, acts as a linker between ATP7B, a major copper chaperone, and the axonal motor proteins, dynein and kinesin II for axonal transport. FIG. 1. See also, Lim C, Cater M, Mercer J, La Fontaine S. Copper-dependent interaction of dynactin subunit p62 with the N terminus of ATP7B but not ATP7A. J Biol Chem. 2006; 281:14006-14, which is incorporated by reference herein.

The interaction between dynein and dynactin has previously been reported to decline with aging; moreover, reducing the expression of dynactin by siRNA in a cell culture system was found to increase both APP levels and beta-cleavage of APP and also resulted in axonal accumulation of tau (Kimura N, et al., "Aging attenuates dynactin-dynein interaction: down-regulation of dynein causes accumulation of endogenous tau and amyloid precursor protein in human neuroblastoma cells." *J Neurosci Res* 85:1909-16 (2007); Kimura N, et al., "Dynein dysfunction induces endocytic pathology accompanied by an increase in Rab GTPases: a potential mechanism underlying age-dependent endocytic dysfunction." *J Biol Chem* 284:31291-302 (2009).

The p62 subunit of dynactin (the subunit found increased in plasma and decreased in brain from cases with AD without CAA) was found to bind ATP7b—a major copper chaperone (Lim C, et al., "Copper-dependent interaction of dynactin subunit p62 with the N terminus of ATP7B but not ATP7A." *J Biol Chem* 281:14006-14 (2006)). The results presented above suggest that dynactin is a link between copper trafficking and axonal transport mechanisms. The proteomic and post-mortem data suggest that lower p62 levels result in axonal trapping of copper and reduced synaptic copper.

EXAMPLE 2

Expression of dynactin subunit p62 in a neuronal cell culture system is targeted for reduction by siRNA. Copper levels are detected to determine whether a decrease in the expression levels of dynactin subunit p62 results in decreased synaptic copper and increased axonal copper, which would suggest that dynactin subunit p62 is directly involved in copper trafficking and axonal transport.

siRNAs to dynactin subunit p62, are commercially available. A preferred source of siRNAs suitable for the purposes of the present invention is Dharmacon. Human dynactin subunit p62 siRNA can also be purchased from Santa Cruz Biotechnology (catalog number sc-35232).

EXAMPLE 3

A proteomic analysis of dynactin p62, which includes quantitation and isolation of abnormal modifications, is performed in samples of frozen AD and control tissue (white and grey matter from frontal, temporal lobes and hippocampus) to analyze dynactin p62's role as a metallochaperone and determine causes for dysfunction in AD. Targeted proteomic assays of dynactin p62 isolates are performed by using database searches to compare predicted amino acid sequences for dynactin p62 and amino acid sequences for dynactin p62 in AD and control tissue.

EXAMPLE 4

Human neuronal cells grown in tissue culture (Clonexpress) differentiate to mature neurons with extensive processes and express neuron specific markers (e.g., Map2, beta tubulin 3). Disruption of dynactin p62 function by RNA interference in neuronal cells provides an in vitro model of abnormal axonal copper trafficking and neurodegeneration associated with Alzheimer's disease.

Human neuronal cells are plated in a 12 well plate and grown to 50% confluence. The neuronal cells are then transfected with commercially available short hairpin RNA (shRNA) lentoviral particle with polycationic facilitation (Polybrene—Santa Cruz Biotechnology) at a concentration of lentoviral particles in the range of 2-10 µg/ml to inhibit dynactin p62 expression. Standard protocols developed by Santa Cruz Biotechnology are followed to obtain neuronal cells with reduced dynactin p62 expression. Stable cloning with dynactin p62 knockdown is confirmed by Western blot of cell lysates.

The effect of complete neuronal dynactin p62 gene silencing on neuron morphology, viability, sphingolipid metabolites, ceramide content and copper trafficking (axonal and synaptic vesicle copper levels) is evaluated over time.

EXAMPLE 5

A mouse model of AD that exhibits reduced levels of synaptic vesicle copper and/or dynactin p62 in the brain after disease onset is identified. A cohort of mice is identified and a candidate agent is administered to a subset of the mice prior to appearance of AD characteristics, while a subset of the mice receives a placebo. The candidate agent may be administered as a single dose, a series of hourly, daily, weekly, bi-weekly, monthly, or yearly doses or continuously for the duration of the test period. At the end of the test period, the levels of synaptic vesicle copper and/or dynactin p62 are measured in the brains of the mice receiving the candidate agent and the mice receiving the placebo. The test period may be ended when about 20%, 30%, 40%, 50%, 60%, 70%, 80% or 90% exhibit symptoms of AD or upon death of the subject. A therapeutic agent that is capable of slowing or preventing the onset of AD is identified where the mice receiving the candidate agent exhibit increased levels of synaptic vesicle copper and/or dynactin p62 compared to the control.

Although several embodiments of the present disclosure have been shown and described by way of example, it would be appreciated by those skilled in the art that changes might be made in these embodiments without departing from the principles and spirit of the disclosure, the scope of which is defined in the claims and their equivalents.

What is claimed is:

1. A kit for detecting Alzheimer's Disease (AD) without cerebral amyloid angiopathy (CAA) in a human subject, said kit comprising:
    a substrate selected from the group consisting of a microtiter plate and a microcolumn;
    an antibody that specifically detects a dynactin subunit p62 polypeptide, wherein the antibody is bound to the substrate;
    a negative reference sample indicative of a subject having AD and CAA;
    a positive control indicative of a subject having AD without CAA, wherein the positive control is indicative of an increased level in plasma of the dynactin subunit p62 polypeptide compared to the level in plasma of the dynactin subunit p62 polypeptide in a sample from a subject having AD and CAA; and
    instructions for using the kit components to determine a level of expression of dynactin subunit p62 and classifying the human subject as having a greater likelihood of AD without CAA if the determined level of expression of dynactin subunit p62 is greater than a predetermined level of expression of dynactin subunit p62 in the negative reference sample.

2. The kit of claim 1, wherein the negative reference sample is derived from a sample comprising plasma.

3. The kit of claim 1, further comprising an additional agent comprising an antibody or fragment thereof that specifically binds a dynactin subunit p62 polypeptide, wherein the additional agent comprises a detectable label.

4. A kit for detecting Alzheimer's Disease (AD) without cerebral amyloid angiopathy (CAA) in a human subject, said kit comprising:
    a substrate selected from the group consisting of a microtiter plate and a microcolumn;

an antibody that specifically detects a dynactin subunit p62 polypeptide, wherein the antibody is bound to the substrate;

a negative reference sample indicative of a subject having AD and CAA; and a positive control indicative of a subject having AD without CAA, wherein the positive control is indicative of an increased level in plasma of the dynactin subunit p62 polypeptide compared to the level in plasma of the dynactin subunit p62 polypeptide in a sample from a subject having AD and CAA.

5. A kit for detecting Alzheimer's Disease (AD) without cerebral amyloid angiopathy (CAA) in a human subject comprising:

a substrate selected from the group consisting of a microtiter plate and a microcolumn;

an antibody that specifically detects a dynactin subunit p62 polypeptide, wherein the antibody is bound to the substrate; and a positive reference control indicative of a human subject having an increased likelihood of having or developing AD without CAA, wherein the positive reference control is indicative of an increased level in plasma of the dynactin subunit p62 polypeptide compared to the level in plasma of the dynactin subunit p62 polypeptide in a sample from a subject having AD and CAA.

6. The kit of claim 5, further comprising a negative reference control indicative of a human subject having AD and CAA.

7. The kit of claim 6, wherein the negative reference control is derived from plasma.

8. The kit of claim 5, further comprising an additional agent comprising an antibody or fragment thereof that specifically binds a dynactin subunit p62 polypeptide, wherein the additional agent comprises a detectable label.

* * * * *